United States Patent [19]

Sakurada et al.

[11] Patent Number: 5,364,969

[45] Date of Patent: Nov. 15, 1994

[54] METHOD FOR THE STABILIZATION OF A SEX PHEROMONE COMPOUND

[75] Inventors: Toyohisa Sakurada; Hiroshi Suzuki; Ryuichi Saguchi, all of Niigata, Japan

[73] Assignee: Shiu-Etsu Chemical Co., Ltd., Tokyo, Japan

[21] Appl. No.: 116,334

[22] Filed: Sep. 3, 1993

[30] Foreign Application Priority Data

Sep. 9, 1992 [JP] Japan .................................. 4-266715

[51] Int. Cl.$^5$ ...................... C07C 45/78; C07C 47/21; C07C 39/08
[52] U.S. Cl. ................................. 568/421; 568/449; 568/702
[58] Field of Search ............... 568/448, 421, 449, 702; 514/310

[56] References Cited

U.S. PATENT DOCUMENTS 4,020,109  4/1977  Fleck et al. ................. 568/421

FOREIGN PATENT DOCUMENTS 4136832  5/1992  Germany ..................... 568/421
0256640 10/1990  Japan ........................ 568/421

*Primary Examiner*—Werren B. Lone
*Attorney, Agent, or Firm*—Henry T. Burke

[57] ABSTRACT

A novel and very effective method is proposed for the stabilization of a higher aliphatic compound having at least one double bond in a molecule such as the sex pheromone compounds of agricultural pest insects used for the elimination of the pest insect by the method of mating disruption. The method comprises admixing the sex pheromone compound with each a specified amount of (a) a specific phenolic compound, e.g., tert-butyl hydroquinone, di-tert-butyl hydroquinone, di-tert-amyl hydroquinone, di-tert-butyl p-cresol, methyl hydroquinone and p-methoxy phenol, as an antioxidant and (b) 2-(2'-hydroxy-3'-tert-butyl-5'-methyl phenyl)-5-chloro benzotriazole in combination.

4 Claims, No Drawings

METHOD FOR THE STABILIZATION OF A SEX PHEROMONE COMPOUND

BACKGROUND OF THE INVENTION

The present invention relates to a method for the stabilization of a sex pheromone compound of pest insects, which is a higher aliphatic con, pound having at least one double bond in a molecule, used for the purpose of elimination of the pest insect by the method of mating disruption between different sexes of the insect species.

One of the serious problems in the agricultural technology against pest insects of agricultural plants in recent years is that, as a consequence of the use of various kinds of agricultural chemicals such as insecticides over many years heretofore, many species of pest insects have acquired resistance against insecticides along with adverse influences of agricultural chemicals not only against the agricultural workers' health but also against the health of the consumers of the agricultural products due to the residual trace amounts of agricultural chemicals therein.

Accordingly, a biological method is now under way of development which utilizes the sex pheromone emitted by the females of the pest insect to attract males of the same species. Namely, the chemical compound of the sex pheromone is chemically synthesized and distributed over the agricultural fields so as to effect disruption of the intersexual communication for mating by means of the sex pheromone resulting in a decreased efficiency of reproduction.

In this method utilizing sex pheromones for the elimination of pest insects, it is essential that the concentration of the sex pheromone compound in the atmospheric air is kept at a controlled level over a period of, for example, several months so that it is usual to prepare and use sustained-release pheromone dispensers containing the sex pheromone compound which is sustainedly released therefrom as is disclosed in Japanese Patent Publication No. 61-16361. Since many of the sex pheromone compounds of the pest insects belonging to the order of Lepidoptera are each a higher aliphatic compound having, for example, 8 to 30 carbon atoms and at least one double bond in a molecule, a serious problem to be solved in the utilization of pheromone dispensers is that the sex pheromone compound is highly susceptible to denaturation or degradation by the reactions of oxidation, isomerization, polymerization and the like at the double bond within a relatively short period of time when the dispensers are kept under outdoor conditions in the agricultural field. This problem is particularly difficult when the sex pheromone compound has a conjugation of double bonds or double bonds of the 1,4-pentadiene type or when it is a higher aliphatic aldehyde compound so that the method of utilization of pheromone dispensers cannot be practically used without solving this problem.

Various attempts and proposals have been made accordingly with an object to stabilize these sex pheromone compounds by the admixture of an antioxidant or ultraviolet absorber with the sex pheromone compound contained in the dispensers. For example, a proposal is made in Journal of Chemical Ecology, volume 14, No. 8, page 1569 (1988) for the use of butyl hydroxytoluene or butyl hydroxyanisole as an antioxidant of sex pheromone compounds and the antioxidation effect thereby can be further enhanced reportedly by the combined use of an ultraviolet absorber such as 2-hydroxy-4-methoxy benzophenone. In fact, the combined use of a specific antioxidant and a specific ultraviolet absorber has a synergistic effect to exhibit good stabilization of several sex pheromone compounds having unsaturation as compared with the single use of either one of these compounds. However, it is quite unclear what particular combinations of an antioxidant compound and an ultraviolet absorbing compound are the most effective for a particular sex pheromone compound.

A proposal is made in Japanese Patent Kokai No. 4-164004 for the combined use of an antioxidant of the hydroquinone type and a benzotriazole compound having a specific substituent group in the molecule as an ultraviolet absorber in order to obtain a high synergistic effect on the stabilization of an unsaturated higher aliphatic compound. While the effect obtained by the combined use of the benzotriazole compound may largely depends on the types and position of the side chain groups to the main chain of the compound, however, nothing is clear on the chemical structure which the benzotriazole compound should have in order to exhibit the highest synergistic effect. Further, Japanese Patent Kokai No. 4-178308 discloses a method for the stabilization of a sex pheromone compound by the combined admixture of an antioxidant and 2-(2'-hydroxy-5'-methylphenyl) benzotriazole and U.S. Pat. No. 4,568,771 discloses admixture of a sex pheromone compound with a benzotriazole compound such as 2-(2'-hydroxy-5'-methylphenyl) benzotriazole.

SUMMARY OF THE INVENTION

The present invention accordingly has an object to provide a novel and improved method for the stabilization of a sex pheromone compound of pest insects which is a higher aliphatic compound having at least one double bond in a molecule free from the above described problems and disadvantages in the prior art methods.

Thus, the method of the present invention for the stabilization of a higher aliphatic compound having from 8 to 30 carbon atoms and at least one double bond in a molecule, known as a sex pheromone compound of agricultural pest insects, comprises: admixing the higher aliphatic compound with (a) a phenolic compound represented by the general formula

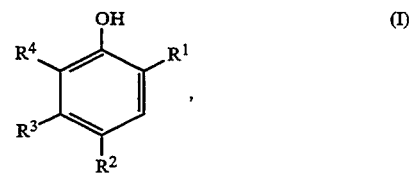

in which $R^1$ is a methyl group, a tert-butyl group or a tert-amyl group, $R^2$ is a hydroxy group, a methyl group or a methoxy group and $R^3$ and $R^4$ are, each independently from the other, a hydrogen atom, a tert-butyl group or a tert-amyl group, and (b) 2-(2'-hydroxy-3'-tert-butyl-5'-methyl phenyl)-5-chloro benzotriazole in combination each in an amount in the range from 0.01 to 20% by weight based on the amount of the higher aliphatic compound.

The above defined inventive method is particularly effective when the higher aliphatic compound is a compound having conjugated double bonds or 1,4-pentadiene-type double bonds or an unsaturated aldehyde compound.

DETAILED DESCRIPTION OF THE PREFERRED EMBODIMENTS

As is described above, the method of the present invention is characterized by the admixture of the higher aliphatic unsaturated compound as a sex pheromone of pest insects with two kinds of specific compounds of which one is the specific phenolic compound represented by the above given general formula (I) as an antioxidant and the other is the specific benzotriazole compound each in a specified amount.

Examples of the phenolic compound represented by the general formula (I) given above include 2,6-di-tert-butyl-p-cresol, 2,5-di-tert-butyl hydroquinone, 2,5-di-tert-amyl hydroquinone, 4-methoxyphenol, methyl hydroquinone, tert-butyl hydroquinone and the like, of which 2,6-di-tert-butyl-p-cresol, 2,5-di-tert-butyl hydroquinone, 2,5-di-tert-amyl hydroquinone and 2-tert-butyl hydroquinone are particularly preferred.

It is known that phenolic compounds as an antioxidant are highly effective for preventing degradation of sex pheromone compounds by the oxidation and polymerization at the double bond as compared with antioxidants of other types such as vitamin E and ethoxyquin, i.e. 6-ethoxy-2,2,4-trimethyl-1,2-dihydroquinoline. Nevertheless, it is generally understood that a sex pheromone compound cannot be fully stabilized under direct sunlight as in the case of outdoor exposure of sex pheromone dispensers when the phenolic antioxidant compound alone is admixed therewith.

The inventors accordingly have conducted extensive investigations in order to uncover a compound which could exhibit a high synergistic effect for the stabilization of a sex pheromone compound when used in combination with a phenolic antioxidant compound and have arrived at a discovery that a great stabilizing effect of sex pheromone compounds can be obtained by the admixture of 2-(2'-hydroxy-3'-tert-butyl-5'-methyl phenyl)-5-chloro benzotriazole in combination with a specific phenolic compound.

The amounts of the phenolic antioxidant compound and the benzotriazole compound added to the sex pheromone compound are each in the range from 0.01 to 20% by weight or, preferably, at least 0.1% by weight based on the sex pheromone compound. When the amount of either one of these two compounds is too small, no sufficient stabilizing effect can be obtained even when the amount of the other compound is adequately high. On the other hand, no further improvement can be obtained in the stabilizing effect even when the amount of either one of these two compounds is increased to exceed the above mentioned upper limit.

Examples of the higher aliphatic unsaturated compounds as a sex pheromone compound of pest insects, to which the inventive method is applicable, include Z-7-dodecenyl acetate, Z-8-dodecenyl acetate, Z-9-dodecenyl acetate, E,Z-7,9-dodecadienyl acetate, Z,Z-7,9-dodecadienyl acetate, E,E-8,10-dodecadienol, E-4-tridecenyl acetate, Z-9-tetradecenyl acetate, Z-9-tetradecenol, Z-11-tetradecenyl acetate, Z-11-tetradecenal, Z-9-hexadecenal, Z-11-hexadecenal, Z,E-9,11-tetradecadienyl acetate, Z,E-9,12-tetradecadienyl acetate, Z-11-hexadecenyl acetate, Z,Z-7,11-hexadecadienyl acetate, E,E,Z-4,6,10-hexadecatrienyl acetate, E,E-10,12-hexadecadienal, Z,Z-3,13-octadecadienyl acetate, E,Z-3,13-octadecadienyl acetate, Z-13-icosen-10-one, E,E,Z-10,12,14-hexadecatrienyl acetate, E,E,Z-10,12,14-hexadecatrienal, E,Z,Z-4,7,18-tridecatrienyl acetate, E,Z-4,7-tridecadienyl acetate, Z,Z,Z-3,6,9-nonadecatriene, Z,Z,Z-3,6,9-icosatriene, Z,Z,Z-3,6,9-henicosatriene and the like.

In particular, the effectiveness of the inventive method for the stabilization of a sex pheromone compound is very remarkable for the sex pheromone compound which is a higher aliphatic compound having two or more double bonds in a molecule or a higher aliphatic aldehyde compound having at least one double bond in a molecule while these unsaturated compounds are known to be notoriously unstable. Further, the stabilizing effect of the inventive method is very significant for higher unsaturated aliphatic compounds having conjugated double bonds including conjugated diene compounds and conjugated triene compounds as well as for the higher aliphatic unsaturated compounds of the 1,4-pentadiene type.

It is optional in practicing the method of the present invention that the sex pheromone compound is admixed with various kinds of known stabilizing agents other than the specific phenolic compound as the antioxidant and 2-(2'-hydroxy-3'-tert-butyl-5'-methyl phenyl)-5-chloro benzotriazole provided that these two essential additives are contained therein in combination each in a specified amount.

In the following, the method of the present invention is described in more detail by way of examples and comparative examples although the scope of the present invention is never limited by these examples in any way.

Examples 1 to 15 and Comparative Examples 1 to 14

A polyethylene tube having an inner diameter of 0.8 mm, outer diameter of 1.4 mm and length of 20 cm was filled with a liquid mixture of 80 mg of a sex pheromone compound and the stabilizing agent or agents in combination as indicated in Tables 1 and 2 given below in an amount indicated there in the brackets in % by weight and the ends of the tube was heat-sealed to prepare a sustained-release pheromone dispenser. A number of the thus prepared pheromone dispensers were kept outdoors in a place under direct sunlight all day long for a period of three months starting in August in Japan. Thereafter, the liquid mixture remaining in the tube was taken out and subjected to the gas chromatographic analysis by the internal standard method for the amount of the sex pheromone compound remaining without being decomposed or degraded. The results were recorded by the ratio of the thus determined remaining amount to the initial amount and are shown in Table 1 for Examples 1 to 15 and in Table 2 for Comparative Examples 1 to 14.

In the following tables showing the formulations of the stabilizing agents and antioxidants in the sex pheromone compounds, the sex pheromone compounds, stabilizing agents and antioxidants as well as other additives used for comparative purpose are referred to by the symbols or abridgments given below.

Sex pheromone compounds
A: E,E-10,12-dodecadienol
B: E,Z-7,9-dodecadienyl acetate
C: Z,E-9,12 -tetradecadienyl acetate
D: Z,Z-7,11 -hexadecadienyl acetate
E: Z-11 -hexadecenal
Stabilizing agent
HBMCBT: 2-(2'-hydroxy-3'-tert-butyl-5'-methyl phenyl)-5-chloro benzotriazole
Antioxidants TBH: tert-butyl hydroquinone
DBH: di-tert-butyl hydroquinone
DAH: di-tert-amyl hydroquinone
BHT: di-tert-butyl p-cresol
MH: methyl hydroquinone
MP: p-methoxy phenol
Other additives
HMBT: 2-(2'-hydroxy-5'-methyl phenyl) benzotriazole
HDBBT: 2-(2'-hydroxy-3',5'-di-tert-butyl phenyl) benzotriazole
HDABT: 2-(2'-hydroxy-3',5'-di-tert-amyl phenyl) benzotriazole
HOBP: 2-hydroxy-4-octoxy benzophenone
VE: vitamin E
EMQ: 6-ethoxy-2,2,4-trimethyl-1,2-dihydroquinoline

TABLE 1

| Example No. | Sex pheromone compound | Stabilizing agents (% by weight) | Remaining amount after exposure (%) |
| --- | --- | --- | --- |
| 1 | A | BHT(2) + HBMCBT(2) | 86 |
| 2 | A | DBH(2) + HBMCBT(2) | 84 |
| 3 | A | BHT(0.5) + HBMCBT(2) | 80 |
| 4 | A | DAH(2) + HBMCBT(2) | 85 |
| 5 | B | BHT(2) + HBMCBT(2) | 77 |
| 6 | B | DBH(2) + HBMCBT(2) | 79 |
| 7 | C | BHT(15) + HBMCBT(5) | 82 |
| 8 | C | TBH(5) + HBMCBT(5) | 74 |
| 9 | C | DAH(5) + HBMCBT(5) | 75 |
| 10 | C | MH(5) + HBMCBT(5) | 70 |
| 11 | D | DBH(1) + HBMCBT(1) | 95 |
| 12 | D | DAH(0.2) + HBMCBT(0.5) | 91 |
| 13 | E | DBH(3) + HBMCBT(3) | 64 |
| 14 | E | DAH(5) + HBMCBT(3) | 67 |
| 15 | E | MP(3) + HBMCBT(3) | 66 |

TABLE 2

| Comparative Example No. | Sex pheromone compound | Stabilizing agents (% by weight) | Remaining amount after exposure (%) |
| --- | --- | --- | --- |
| 1 | A | VE(2) + HBMCBT(2) | 58 |
| 2 | A | EMQ(5) + HBMCBT(2) | 51 |
| 3 | A | BHT(5) | 42 |
| 4 | A | HBMCBT(2) | 36 |
| 5 | B | BHT(2) + HOBP(2) | 51 |
| 6 | B | BHT(2) + HMBT(2) | 62 |
| 7 | B | DBH(2) + HDABT(2) | 59 |
| 8 | C | none | 0 |
| 9 | C | VE(5) + HOBP(5) | 22 |
| 10 | C | BHT(5) + HDBBT(5) | 43 |
| 11 | C | TBH(5) + HMBT(2) | 53 |
| 12 | D | VE(1) + HOBP(5) | 79 |
| 13 | E | BHT(3) + HDABT(3) | 52 |
| 14 | E | TBH(3) + HDBBT(3) | 55 |

What is claimed is:

1. A method for the stabilization of a higher aliphatic compound having the activity of an insect sex pheromone containing from about 8 to 30 carbon atoms and at least one double bond in the molecule which comprises: admixing the higher aliphatic compound with (a) a phenolic compound represented by the general formula

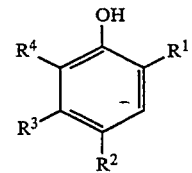

in which $R^1$ is a methyl group, a ter-butyl group or a tert-amyl group, $R^2$ is hydroxy group, a methyl group or a methoxy group and $R^3$ and $R^4$ are, each independently from the other, a hydrogen atom, a tert-butyl group or a tert-amyl group, and (b) 2-(2'-hydroxy-3'tert-butyl-5'-methyl phenyl)-5-chloro benzotriazole in combination each in an amount in the range of from 0.01 to 20% be weight based on the amount of the higher aliphatic compound.

2. The method for the stabilization of a higher aliphatic compound having at least one double bond in a module as claimed in claim 1 in which the phenolic compound is selected from the group consisting of 2,6-di-tert-butyl p-cresol, 2,5-di-tert-butyl hydroquinone, 2,5-di-tert-amyl hydroquinone and 2-tert-butyl hydroquinone.

3. The method for the stabilization of a higher aliphatic compound having the activity of an insect pheromone containing from about 8 to 30 carbon atoms and conjugated double bonds in the molecule which comprises: admixing the higher aliphatic compound with (a) a phenolic compound represented by the general formula

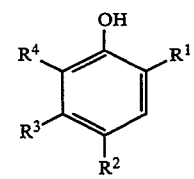

in which $R^1$ is a methyl group, a tert-butyl group or a tert-amyl group, $R^2$ is a hydroxy group, a methyl group or a methoxy group and $R^3$ and $R^4$ are, each independently from the other, a hydrogen atom, a tert-butyl group or a tert-amyl group, and (b) 2-(2'-hydroxy-3'-tert-butyl-5'-methyl phenyl)-5-chloro benzotriazole in combination each in an amount in the range from 0.01 to 20% by weight based on the amount of the higher aliphatic compound.

4. A method for the stabilization of a higher aliphatic aldehyde compound having the activity of an insect pheromone containing from about 8 to 30 carbon atoms and at least one double bond in the molecule which comprises: admixing the higher aliphatic compound with (a) a phenolic compound represented by the general formula

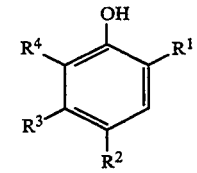

in which $R^1$ is a methyl group, a tert-butyl group or a tert-amyl group, $R^2$ is a hydroxy group, a methyl group or a methoxy group and $R^3$ and $R^4$ are, each independently from the other, a hydrogen atom, 3-tert-butyl group or tert-amyl group, and (b) 2-(2'-hydroxy-3'-tert-butyl-5'methyl phenyl)-5-chloro benzotriazole in combination each in an amount in the range from 0.01 to 20% by weight based on the amount of the higher aliphatic compound.

* * * * *